United States Patent [19]

Wayne

[11] Patent Number: 5,715,033
[45] Date of Patent: Feb. 3, 1998

[54] APPARATUS FOR EXAMINING IN CLOSE PROXIMITY AN EYE OF A USER

[76] Inventor: Steven L. Wayne, 37534 Hudson St., Palmdale, Calif. 93552

[21] Appl. No.: 785,775

[22] Filed: Jan. 21, 1997

[51] Int. Cl.[6] .............................. G02C 3/10; G02C 3/00
[52] U.S. Cl. .................................... 351/205; 351/200
[58] Field of Search .................................. 351/200, 205, 351/218, 227, 246

[56] References Cited

U.S. PATENT DOCUMENTS 4,934,809  6/1990  Volk ......................................... 351/205

Primary Examiner—Hung X. Dang

[57] ABSTRACT

An apparatus for examining in close proximity an eye of a user including a mirror with a glass disk having a diameter of less than 50 mm. The glass disk has a front face with a concave surface, a rear face with a convex surface, and a periphery formed therebetween. The mirror further includes a film with a first opaque side and a second reflective side. The film is situated on the rear face of the glass disk such that the reflective side thereof is in communication with the entire convex surface. Further provided is a mount for securing about the mirror for gripping purposes. By this structure, the mirror may be situated in the front of an eye of a user for allowing the careful examination thereof.

3 Claims, 3 Drawing Sheets

APPARATUS FOR EXAMINING IN CLOSE PROXIMITY AN EYE OF A USER

BACKGROUND OF THE INVENTION

1. Field of the Invention

The present invention relates to a apparatus for examining in close proximity an eye of a user and more particularly pertains to allowing a user to examine his own eye despite defects in vision.

2. Description of the Prior Art

The use of concave mirrors is known in the prior art. More specifically, concave mirrors heretofore devised and utilized for the purpose of manipulating an image are known to consist basically of familiar, expected and obvious structural configurations, notwithstanding the myriad of designs encompassed by the crowded prior art which have been developed for the fulfillment of countless objectives and requirements.

By way of example, the prior art includes U.S. Pat. No. 4,062,625 to Fleishman et al.; U.S. Pat. No. 5,072,104 to Tatian; U.S. Pat. No. 4,227,780 to Ohta et al.; U.S. Pat. No. 4,887,897 to Nose et al.; U.S. Pat. No. 5,383,053 to Hegg et al.; and U.S. Pat. No. 4,738,521 to Volk.

In this respect, the apparatus for examining in close proximity an eye of a user according to the present invention substantially departs from the conventional concepts and designs of the prior art, and in so doing provides an apparatus primarily developed for the purpose of allowing a user to examine his own eye despite defects in vision.

Therefore, it can be appreciated that there exists a continuing need for a new and improved apparatus for examining in close proximity an eye of a user which can be used for allowing a user to examine his own eye despite defects in vision. In this regard, the present invention substantially fulfills this need.

SUMMARY OF THE INVENTION

In view of the foregoing disadvantages inherent in the known types of concave mirrors now present in the prior art, the present invention provides an improved apparatus for examining in close proximity an eye of a user. As such, the general purpose of the present invention, which will be described subsequently in greater detail, is to provide a new and improved apparatus for examining in close proximity an eye of a user which has all the advantages of the prior art and none of the disadvantages.

To attain this, the present invention essentially comprises a mirror having a glass disk with a diameter of less than 50 mm. As best shown in FIG. 5, the glass disk of the mirror has a front face with a concave surface, a rear face with a convex surface, and a periphery formed therebetween. For reflecting purposes, the mirror further has a film with a first opaque side and a second reflective side. The film is situated on the rear face of the glass disk such that the reflective side thereof is in communication with the entire convex surface. Associated therewith is a mount with a U-shaped configuration formed of a resilient material from the group including plastic. The mount has a semicircular member which has a periphery extending a distance slightly greater than 79 mm. The semicircular member further has a pair of integral lips extending radially inwardly from opposite side edges thereof a distance less than 12.7 mm. Such lips define a groove in which the mirror may be removably situated in a secure manner. The mount further has a cylindrical post integrally coupled at an end thereof to a central extent of an outer surface of the semicircular member for gripping purposes.

There has thus been outlined, rather broadly, the more important features of the invention in order that the detailed description thereof that follows may be better understood, and in order that the present contribution to the art may be better appreciated. There are, of course, additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

It is therefore an object of the present invention to provide a new and improved apparatus for examining in close proximity an eye of a user which has all the advantages of the prior art concave mirrors and none of the disadvantages.

It is another object of the present invention to provide a new and improved apparatus for examining in close proximity an eye of a user which may be easily and efficiently manufactured and marketed.

It is a further object of the present invention to provide a new and improved apparatus for examining in close proximity an eye of a user which is of a durable and reliable construction.

An even further object of the present invention is to provide a new and improved apparatus for examining in close proximity an eye of a user which is susceptible of a low cost of manufacture with regard to both materials and labor, and which accordingly is then susceptible of low prices of sale to the consuming public, thereby making such apparatus for examining in close proximity an eye of a user economically available to the buying public.

Still yet another object of the present invention is to provide a new and improved apparatus for examining in close proximity an eye of a user which provides in the apparatuses and methods of the prior art some of the advantages thereof, while simultaneously overcoming some of the disadvantages normally associated therewith.

Still another object of the present invention is to allow a user to examine his own eye despite defects in vision.

Another object of the present invention is to provide a unique mounting mechanism for the optic mirror.

Lastly, it is an object of the present invention to provide a new and improved apparatus for examining in close proximity an eye of a user including a mirror with a glass disk having a diameter of less than 50 mm. The glass disk has a front face with a concave surface, a rear face with a convex surface, and a periphery formed therebetween. The mirror further includes a film with a first opaque side and a second reflective side. The film is situated on the rear face of the glass disk such that the reflective side thereof is in communication with the entire convex surface. Further provided is a mount for securing about the mirror for gripping purposes. By this structure, the mirror may be situated in the front of an eye of a user for allowing the careful examination thereof.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

Similar reference characters refer to similar parts throughout the several views of the drawings.

DESCRIPTION OF THE PREFERRED EMBODIMENT

Figure 1:
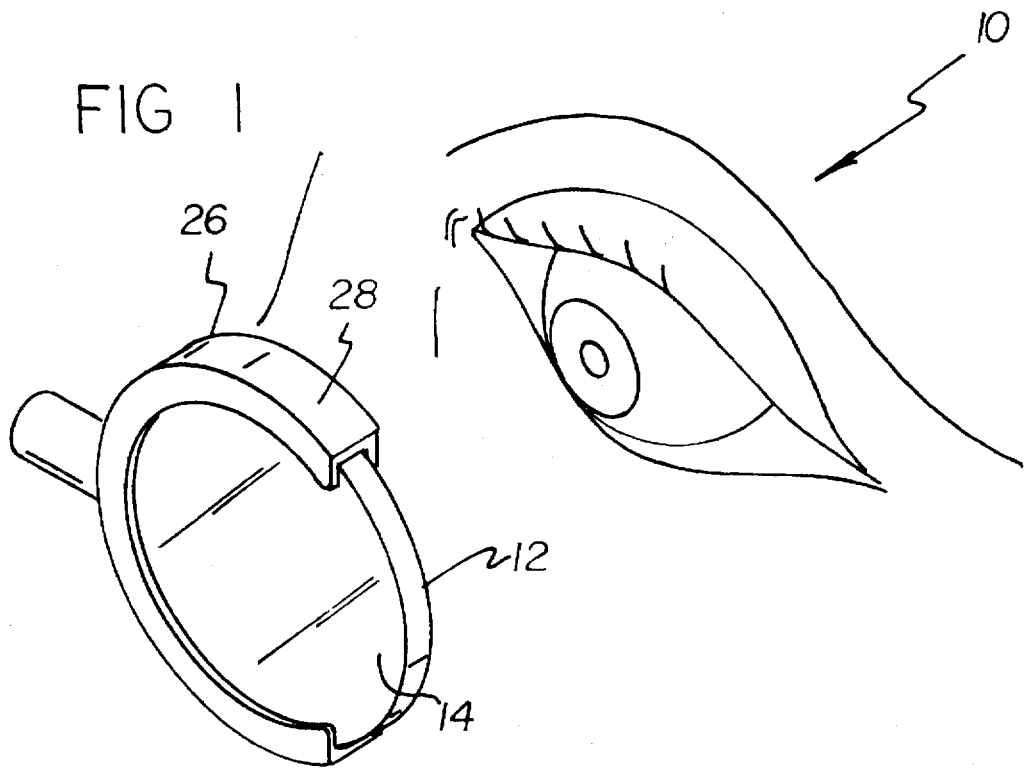
FIG. 1 is a perspective illustration of the preferred embodiment of the apparatus for examining in close proximity an eye of a user constructed in accordance with the principles of the present invention.
Figure 2:
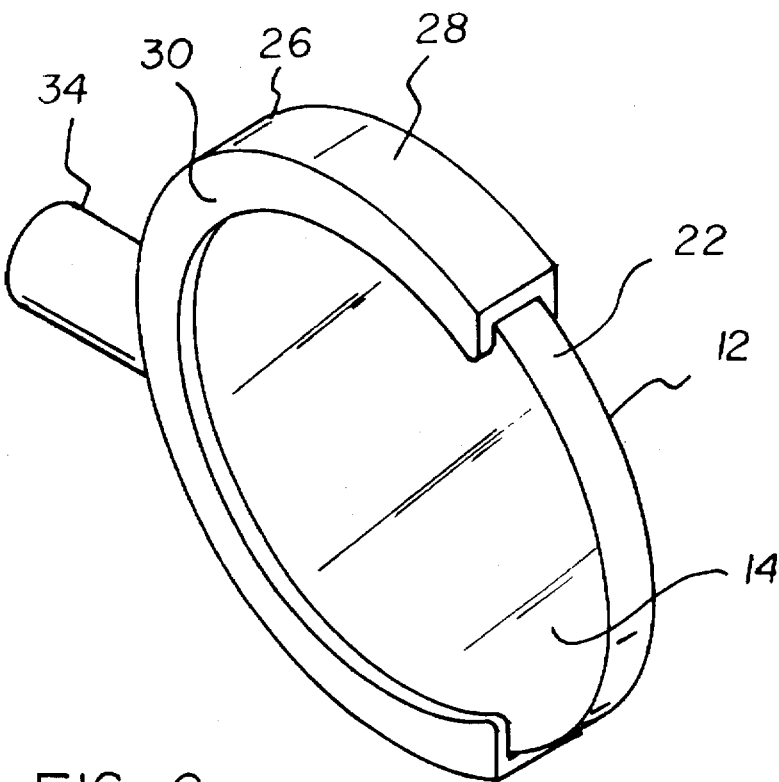
FIG. 2 is a perspective illustration of the present invention.
Figure 3:
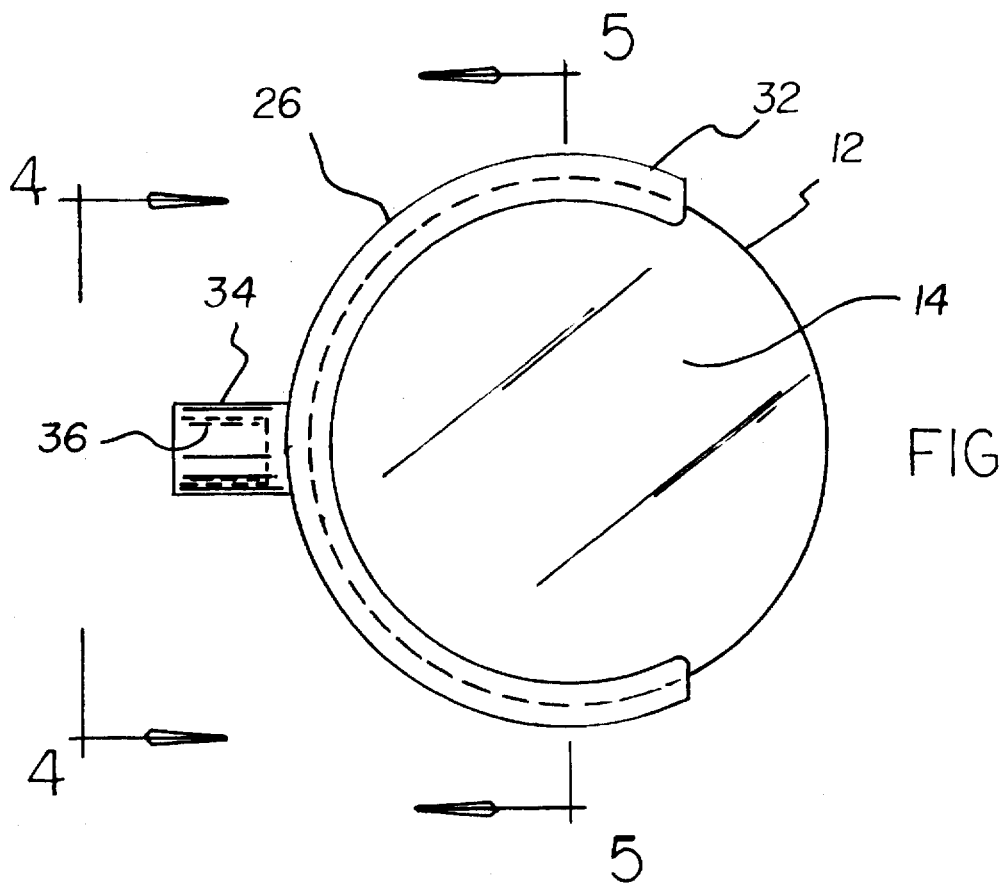
FIG. 3 is a front view of the present invention.
Figure 4:
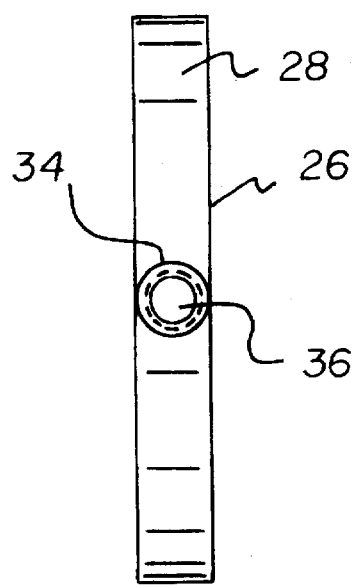
FIG. 4 is a side view of the present invention.

With reference now to the drawings, and in particular to FIG. 1 thereof, a new and improved apparatus for examining in close proximity an eye of a user embodying the principles and concepts of the present invention and generally designated by the reference numeral 10 will be described.

The present invention, the new and improved apparatus for examining in close proximity an eye of a user, is comprised of a plurality of components. Such components in their broadest context include a concave mirror and a mount. Such components are individually configured and correlated with respect to each other so as to attain the desired objective.

Figure 5:
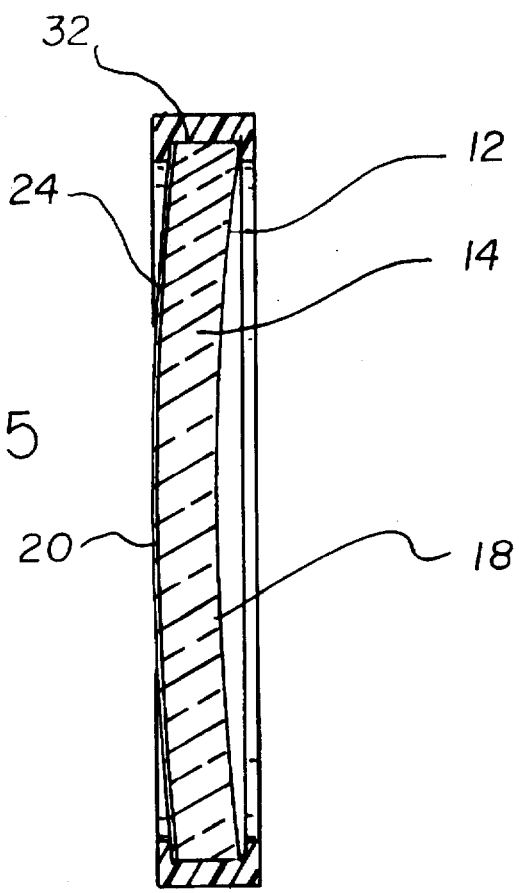
FIG. 5 is a cross-sectional view of the present invention taken along line 5—5 shown in FIG. 3.
Figure 6:
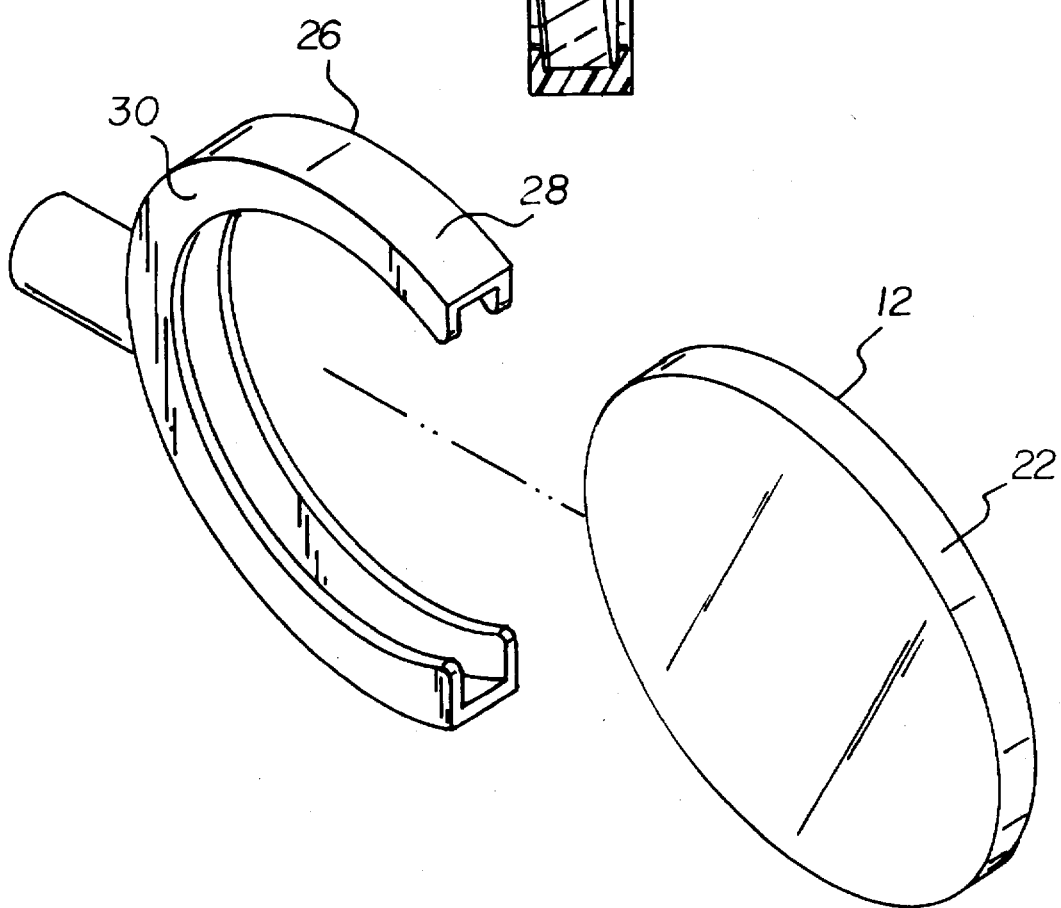
FIG. 6 is an exploded view of the present invention showing the decoupling of the mount and mirror.

More specifically, it will be noted that the system 10 of the present invention includes a mirror 12 having a glass disk 14 with a diameter of less than 50 mm. As best shown in FIG. 5, the glass disk of the mirror has a front face 18 with a concave surface, a rear face 20 with a convex surface, and a periphery 22 formed therebetween. For reflecting purposes, the mirror further has a film 24 with a first opaque side and a second reflective side. The film is situated on the rear face of the glass disk such that the reflective side thereof is in communication with the entire convex surface. Ideally, the mirror has a thickness of approximately 12.7 mm. It should be noted that the specific diameter and thickness of the glass disk of the mirror is critical for equipping the rear face with an optimal range of radii of curvatures, for reasons that will be come apparent later.

Associated therewith is a mount 26 with a U-shaped configuration formed of a resilient material from the group including plastic. The mount has a semicircular member 28 which has a periphery extending a distance slightly greater than 79 mm and no more than 118 mm. The semicircular member further has a pair of integral lips 30 extending radially inwardly from opposite side edges thereof a distance less than 12.7 mm. Such lips define a groove 32 in which the mirror may be removably situated in a secure manner.

The length limitation of the semicircular member 28 is critical in that it is equal to ½ the circumference of the mirror as dictated by the equation circumference=diameter* π. By ensuring that the length of the semicircular member is greater than half of the circumference of the mirror, the mirror is ideally secured within the groove of the mount. It should be noted that the resilient nature of the semicircular member also contributes to convenient insertion and removal of the mirror therein. This is afforded by ends of the semicircular member being capable of being biased slightly apart during the insertion and removal of a mirror. The foregoing features allow convenient replacement of the mirror and further allow mirrors with various optic features to be utilized when examining one's own eye.

The mount further has a cylindrical post 34 integrally coupled at an end thereof to a central extent of an outer surface of the semicircular member for gripping purposes. The cylindrical post is further equipped with a threaded bore 36 formed concentrically therein. Such bore allows the selective coupling with additional handling mechanisms.

In use, the mirror may be situated in the front of an eye of a user for allowing carefully examination thereof. The concave nature of the mirror allows a user to carefully examine the eye despite any defect in vision that he or she might have. As an option, mirrors of various radii of curvatures may be utilized to accommodate users of different vision defects.

As to the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by LETTERS PATENT of the United States is as follows:

1. A new and improved apparatus for examining in close proximity an eye of a user comprising, in combination:

a mirror including glass disk having a diameter of less than 50 mm, the glass disk having a front face with a concave surface, a rear face with a convex surface, and a periphery formed therebetween, the mirror further having a film with a first opaque side and a second reflective side, the film situated on the rear face of the glass disk such that the reflective side thereof is in communication with the entire convex surface; and a mount with a U-shaped configuration formed of a resilient material from the group including plastic, the mount having a semicircular member which has a periphery extending a distance slightly greater than 79 mm, the semicircular member having a pair of lips extending radially inwardly from opposite side edges thereof a distance less than 12.7 mm defining a groove in which the mirror may be removably situated in a secure manner, the mount further having a cylindrical post integrally coupled at an end thereof to a central extent of an outer surface of the semicircular member for gripping purposes;

whereby the mirror is situated in the front of an eye of a user for allowing carefully examination thereof.

2. A apparatus for examining in close proximity an eye of a user comprising:

a mirror including glass disk having a diameter of less than 50 mm, the glass disk having a front face with a concave surface, a rear face with a convex surface, and a periphery formed therebetween, the mirror further having a film with a first opaque side and a second reflective side, the film situated on the rear face of the glass disk such that the reflective side thereof is in communication with the entire convex surface; and a mount means for securing about the mirror for gripping purposes;

whereby the mirror is situated in the front of an eye of a user for allowing carefully examination thereof.

3. A apparatus for examining in close proximity an eye of a user as set forth in claim 2 wherein the mounting means includes a mount with a U-shaped configuration formed of a resilient material from the group including plastic, the mount having a semicircular member which has a periphery extending a distance slightly greater than 79 mm, the semicircular member having a pair of lips extending radially inwardly from opposite side edges thereof a distance less than 12.7 mm defining a groove in which the mirror may be removably situated in a secure manner, the mount further having a cylindrical post integrally coupled at an end thereof to a central extent of an outer surface of the semicircular member for gripping purposes.

* * * * *